United States Patent
Vastano (10) Patent No.: US 7,201,726 B2
(45) Date of Patent: Apr. 10, 2007

(54) METHOD FOR PHYSIOLOGICAL VOLUME MEASUREMENT AND ANALYSIS

(76) Inventor: Gaetano F. Vastano, P.O. Box 5188, Kent, WA (US) 98064-5188

( * ) Notice: Subject to any disclaimer, the term of this patent is extended or adjusted under 35 U.S.C. 154(b) by 382 days.

(21) Appl. No.: 10/390,491

(22) Filed: Mar. 17, 2003

(65) Prior Publication Data
US 2004/0186395 A1 Sep. 23, 2004

(51) Int. Cl.
A61B 5/117 (2006.01)
A61B 5/103 (2006.01)

(52) U.S. Cl. .................................. 600/587
(58) Field of Classification Search ............. 600/587, 600/592, 594, 507; 33/511–512; 607/88
See application file for complete search history.

(56) References Cited

U.S. PATENT DOCUMENTS

| 3,847,142 | A | * | 11/1974 | Williams et al. | ............ 600/507 |
| 5,891,059 | A | * | 4/1999 | Anderson | ............ 600/587 |
| 6,413,212 | B1 | * | 7/2002 | Raab | ............ 600/300 |
| 2003/0171795 | A1 | * | 9/2003 | Walmsley et al. | ............ 607/88 |

FOREIGN PATENT DOCUMENTS

DE 3535270 A1 * 4/1987

OTHER PUBLICATIONS

Stanton et al, Validation of an Optoelectric Limb Volumeter (Perometer), 1997, Lymphology 30, Abstract.*

* cited by examiner

*Primary Examiner*—Max F. Hindenburg
*Assistant Examiner*—Brian Szmal
(74) *Attorney, Agent, or Firm*—John Wiley Horton (57) ABSTRACT

A repeatable patient-specific measurement technique, along with a technique for analyzing the data obtained. The process employs common anatomical reference points to guide the clinician performing the measurements. The measurements taken are logged into a database using a standard format. A volume corresponding to the area measured is then calculated. The series of measurements can be accurately repeated during subsequent evaluations of the same patient. Subsequent volume calculations are also made so that the volume of the measured region can be tracked over time. The volumetric information is then used to evaluate certain patient-specific criteria such as efficacy of treatment and accuracy of diagnosis. The volumetric information can also be correlated to the patient's region of origin, age, sex, ethnicity, occupation and the like. The process is preferably performed using computer software to record the measurement techniques, calculate the volumes, and present the data in a variety of numerical and graphical formats. Treatments employed—as well as physical observations made—can be tied to the measurements in the database, so that a clinician can evaluate the efficacy of various treatments. Other information can also be stored in the database to allow the aforementioned correlative analysis.

11 Claims, 14 Drawing Sheets

| | New | | | Date: |
|---|---|---|---|---|
| | Patient Name: Joliet, Megan | | 83 | Time: 44 |

2/20/2003 12:00:00AM

Body Area 42 — ☐ Affected Right Arm ☐

Measurements are in Centimeters

| 40 Intervals | | Circumference Measurement |
|---|---|---|
| A - B | 3 | |
| B - C | 3 | |
| C - D | 1 | |
| D - E | 1 | |
| E - F | 1 | |
| F - G | 1 | |
| G - H | 1 | |
| H - I | 3 | |
| I - J | 3 | |
| J - K | 3 | |
| K - L | 3 | |
| L - M | 3 | |
| M - N | 3 | |
| N - O | 3 | |
| O - P | 3 | |
| P - Q | 3 | |
| Q - R | 3 | |
| R - S | 3 | |
| S - T | 3 | |
| T - U | 3 | |
| U - V | 3 | |

46

| Treatments | | |
|---|---|---|
| | Code | Duration (minutes) |
| Primary | | |
| Secondary | | |
| Third | | |
| Fourth | | |
| Fifth | | |

Notes 48

Patient Name: Joliet, Megan          Body Area: Affected Right Arm

Date of Measurement: 2/5/2003       7:49:09PM       Measurements are in Centimeters

| Point | Measurements | Circumference @ | Unit of Measure Conversions | | Segmental Volume Liters | Percent change from First Treatment % units | | | Previous Date |
|---|---|---|---|---|---|---|---|---|---|
| A | 0 cm. Distal end of ulna styloid process to axilla | 23.22 cm. | AB | 172.88 | 0.17 | -27.69 | -0.07 | Liters | 0.04 |
| B | 4.00 cm. Distal end of ulna styloid process to axilla | 23.39 cm. | BC | 137.10 | 0.14 | -37.40 | -0.08 | Liters | -1.86 |
| C | 8.00 cm. Distal end of ulna styloid process to axilla | 18.00 cm. | CD | 115.02 | 0.12 | -37.27 | -0.07 | Liters | -4.08 |
| D | 12.00 cm. Distal end of ulna styloid process to axilla | 20.00 cm. | DE | 143.56 | 0.14 | -26.39 | -0.05 | Liters | -2.05 |
| E | 16.00 cm. Distal end of ulna styloid process to axilla | 22.45 cm. | EF | 179.34 | 0.18 | -19.50 | -0.04 | Liters | -1.90 |
| F | 20.00 cm. Distal end of ulna styloid process to axilla | 25.00 cm. | FG | 232.47 | 0.23 | -8.84 | -0.02 | Liters | -3.08 |
| G | 24.00 cm. Distal end of ulna styloid process to axilla | 29.00 cm. | GH | 267.70 | 0.27 | -16.48 | -0.05 | Liters | -3.03 |
| H | 28.00 cm. Distal end of ulna styloid process to axilla | 29.00 cm. | HI | 306.32 | 0.31 | -29.06 | -0.13 | Liters | -2.49 |
| I | 32.00 cm. Distal end of ulna styloid process to axilla | 33.00 cm. | IJ | 366.98 | 0.37 | -29.20 | -0.15 | Liters | -2.26 |
| J | 36.00 cm. Distal end of ulna styloid process to axilla | 34.90 cm. | JK | 366.98 | 0.37 | -30.91 | -0.16 | Liters | -2.99 |
| K | 40.00 cm. Distal end of ulna styloid process to axilla | 33.00 cm. | KL | 336.24 | 0.34 | -26.76 | -0.12 | Liters | -3.48 |
| L | 44.00 cm. Distal end of ulna styloid process to axilla | 32.00 cm. | LM | 326.97 | 0.33 | -22.70 | -0.10 | Liters | -2.78 |
| M | 48.00 cm. Distal end of ulna styloid process to axilla | 32.10 cm. | MN | 316.88 | 0.32 | -26.69 | -0.12 | Liters | -2.49 |
| N | 52.00 cm. Distal end of ulna styloid process to axilla | 31.00 cm. | NO | 316.88 | 0.32 | -28.27 | -0.12 | Liters | -2.49 |
| O | | 32.10 cm. | OP | | | | | | |
| P | | | PQ | | | | | | |
| Q | | | QR | | | | | | |
| R | | | RS | | | | | | |
| S | | | ST | | | | | | |
| T | | | TU | | | | | | |
| U | | | UV | | | | | | |
| V | | | Total Volume | 3,585.32 cubic cm | 3.59 Liters | -26.41 % | -1.29 | Liters | -2.58 % |

Notes

Ms. J indicated her arm feels stronger. She has been wearing the compression wraps and feel that they are helping

52

Treatments

| Category | Treatments | Duration(min) |
|---|---|---|
| Primary | 97110 | 40 |
| Secondary | 97535 | 30 |
| Third | 97112 | 25 |
| Fourth | 97140 | 15 |
| Fifth | 97150 | 10 |

FIG.10

*Quantitative Volumetric Outcome Report*

Report Date: 2/20/2003

| Patient Name: | Joliet, Megan | Social Security Number: | 064-45-3121 |

| Sex: | Female | | Occupation: | 654 |
| Age: | 55 | | | |
| Home Phone: | (212) 333-1444 | | Initial eval date: | 1/27/2003 |
| Work Phone: | (212) 666-1313 ext. 67 | | Surgery Date: | 1/30/2003 |
| Race: | Hispanic or Latino | | Therapists: | |
| Ethnicity: | Hispanic or Latino | | | Taylor, Cynthia |
| Physicians: | | | | |

Diagnosis:

675.45

Primary Insurance:     Secondary Insurance

Blue Cross

Report Data Selection Criteria

All patient measurements for the selected body part, Affected Right Arm

This patient was treated for 7 sessions

*Volumes ver 1.0*

METHOD FOR PHYSIOLOGICAL VOLUME MEASUREMENT AND ANALYSIS

CROSS-REFERENCES TO RELATED APPLICATIONS

Not Applicable.

STATEMENT REGARDING FEDERALLY SPONSORED RESEACH OR DEVELOPMENT

Not Applicable.

MICROFICHE APPENDIX

Not Applicable.

BACKGROUND OF THE INVENTION

1. Field of the Invention

This invention relates to the field of medicine. More specifically, the invention comprises a method for accurately determining the volume of portions of the human body, for use in treating swelling disorders and other medical conditions, as well as facilitating analysis of the data obtained.

2. Description of the Related Art

In assessing and monitoring certain conditions of the human body, it is often helpful to know the volume of a portion or portions of the body. One example of a condition of interest is the presence of edema. "Edema" is generally defined as the retention of excess fluid within the tissues of the body. It typically results in swelling of the affected area.

Clinicians are trained to observe the presence of edema. These observations have not traditionally been reliably quantified, however. In some instances a measurement of circumference or chord length of the affected area is made. These measurements can give qualitative results regarding changes over time—such as the fact that the edema in one particular area has improved. However, such local measurements do little to aid the understanding of edema over a segmental region, broad area, or the body as a whole.

To document the progress of treatment it is often necessary to evaluate the edema over time. It is very difficult to repeat one or two measurements taken of a particular location, since they may not be tied to a convenient anatomical reference. Thus, the traditional approaches may not be able to provide repeatable results even in terms of a qualitative change over time. If, as an example, a clinician measures the diameter of a patient's forearm between the wrist and the elbow, it may be difficult to repeat the position of the measurement when the patient is back in the office a week or two later. If a different diameter is then observed, the clinician will not know whether it represents a change in the patient's condition or merely an artifact of the measurement process.

In contrast, the process disclosed herein generates repeatable results from visit to visit and clinician to clinician. Using the process, volumetric data from a specific patient can be accurately obtained and thereafter used to evaluate the treatments administered.

BRIEF SUMMARY OF THE INVENTION

The present invention comprises a repeatable patient-specific measurement technique, along with a technique for analyzing the data obtained. The inventive process employs common anatomical reference points to guide the clinician performing the measurements. The measurements taken are logged into a database using a standard format. A volume corresponding to the area measured is then calculated. The series of measurements can be accurately repeated during subsequent evaluations of the same patient. Subsequent volume calculations are also made so that the volume of the measured region can be tracked over time. The volumetric information is then used to evaluate certain patient-specific criteria such as efficacy of treatment and the relationship of edema to the patient diagnosis. The volumetric information can also be correlated to the patient's region of origin, age, sex, ethnicity, occupation and the like.

The process is preferably performed using computer software to record the measurement techniques, calculate the volumes, and present the data in a variety of numerical and graphical formats. Treatments employed—as well as physical observations made—can be tied to the measurements in the database, so that a clinician can evaluate the efficacy of various treatments. Other information can also be stored in the database to allow the aforementioned correlative analysis.

BRIEF DESCRIPTION OF THE SEVERAL VIEWS OF THE DRAWINGS

FIG. 10 is a view of a sample data sheet.

REFERENCE NUMERALS IN THE DRAWINGS 10 central axis
12 external start point
14 faceted volume
16 arm
18 ulna styloid process
20 axilla
28 atypical leg
30 computed volume
32 lower plane
34 upper plane
36 measurement input form
38 physiological reference
40 length input
42 circumference input
44 date/time entry
46 treatment input 48 notation input
50 measurement guide
52 sample data sheet
54 graphical data presentation
60 chord length
62 contoured object
C1 first circumference
C2 second circumference
C3 third circumference
C4 fourth circumference
C5 fifth circumference
C6 sixth circumference
C7 seventh circumference
C8 eighth circumference
C9 ninth circumference
C10 tenth circumference
L1 first length
L2 second length
L3 third length
L4 fourth length
L5 fifth length
V1 first volume
V2 second volume
V3 third volume
V4 fourth volume
V5 fifth volume
V6 sixth volume
V7 seventh volume
V8 eighth volume
V9 ninth volume

DETAILED DESCRIPTION OF THE INVENTION

Figure 1:
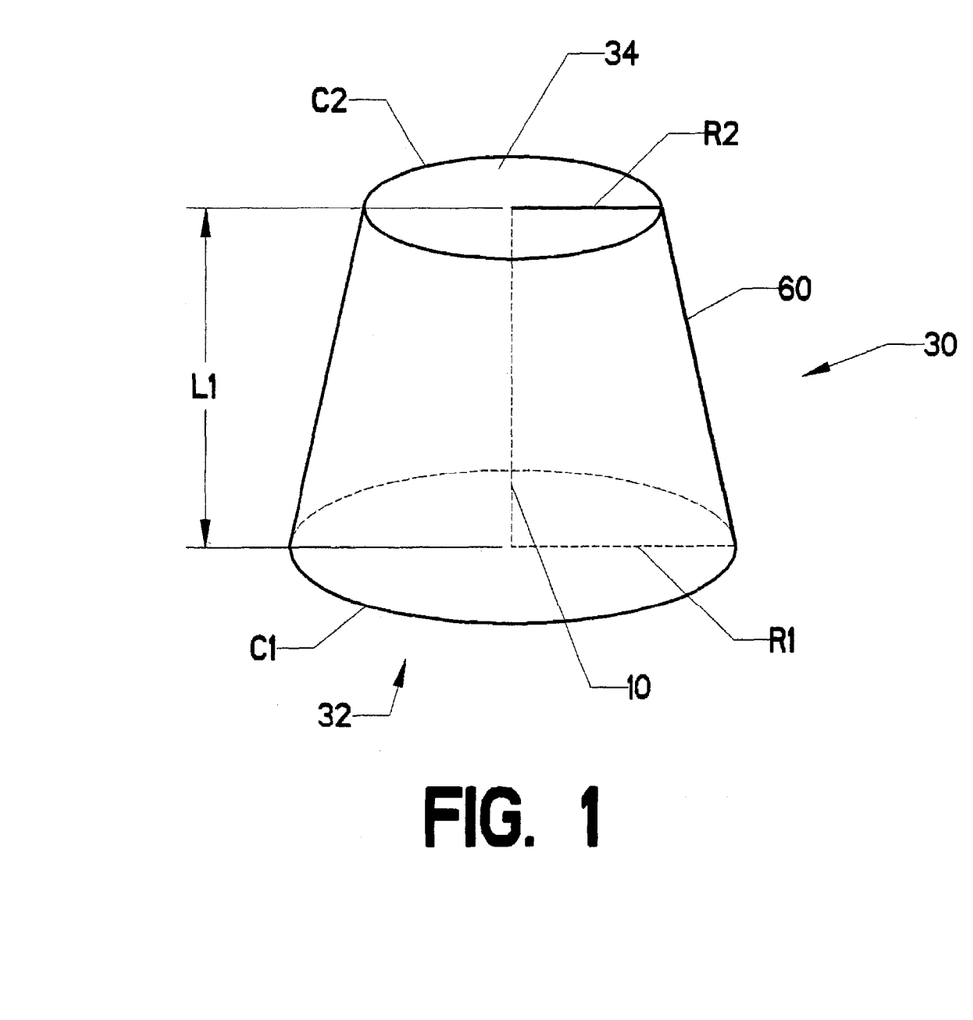
FIG. 1 is an isometric view, showing a truncated cone.

FIG. 1 shows the basic geometrical element used in the present invention—a truncated right cone. This object is defined by lower plane 32, having first circumference C1, and upper plane 34, having second circumference C2. Upper plane 34 is offset from lower plane 32 a first length L1 along central axis 10. The radius corresponding to each circumference can be found using the following expression $R=C/(2\times\Pi)$, where "C" represents the circumference and "R" represents the corresponding radius.

A radius R1 corresponding to first circumference C1 and a radius R2 corresponding to second circumference C2 are thereby computed. The volume of the truncated cone can then be determined using the expression:

$$V = \tfrac{1}{3} \times \Pi \times L1 \times (R1^2 + R2^2 + R1 \times R2)$$

Thus, by knowing the values for C1, C2, and L1, one can easily determine a value for computed volume 30. These geometric principles are essential to the inventive process herein disclosed, for the simple truncated cone can be used to approximate many types of complex geometry.

Figure 2:
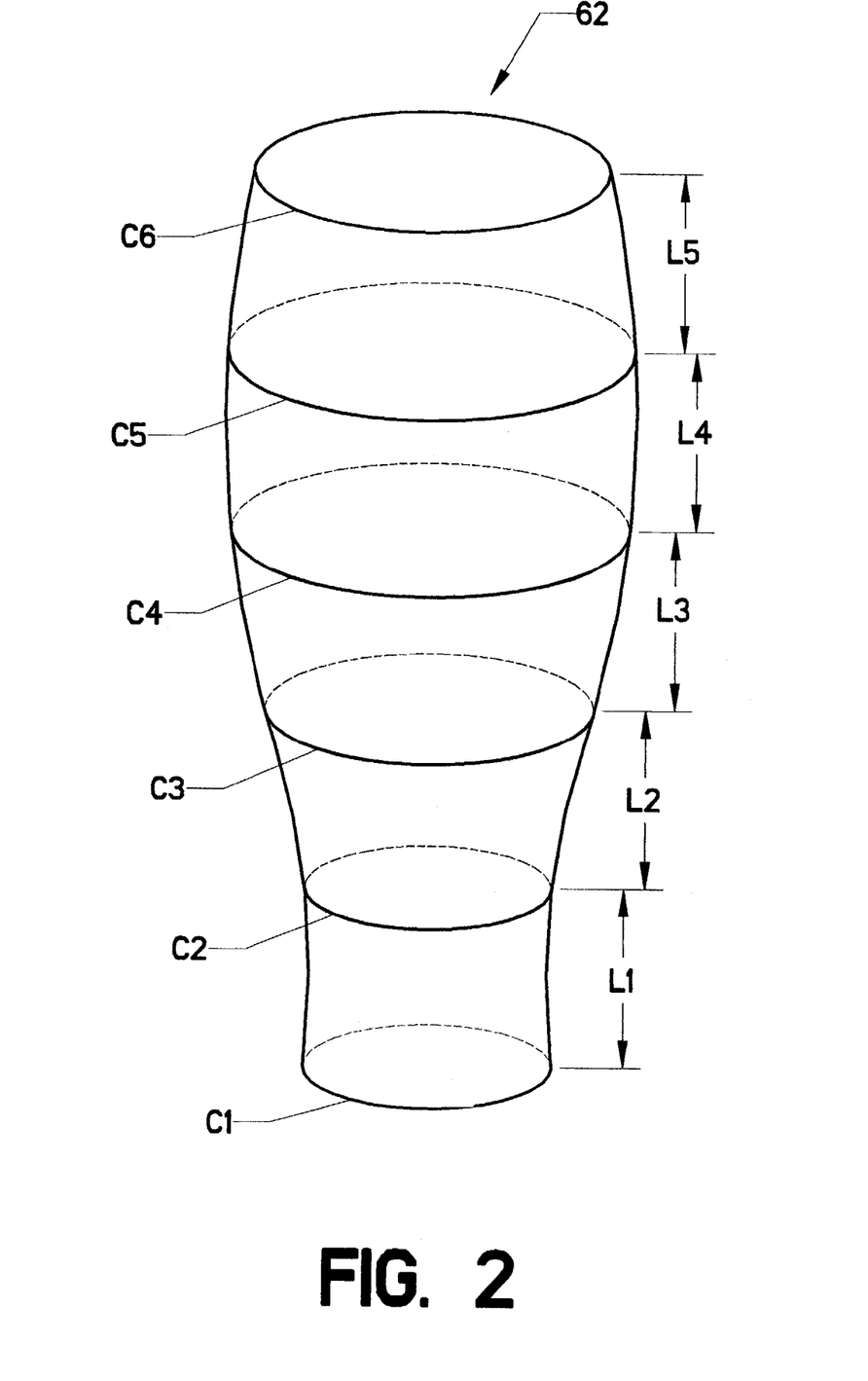
FIG. 2 is an isometric view, showing an example of contoured geometry.

FIG. 2 depicts contoured object 62, which has a complex curved shape. Like the truncated cone of FIG. 1, it has a central axis. In order to determine its volume, the user first selects an external start point. A circumference measurement—C1—is taken at this point. The user then moves along the object's surface, in a direction approximately perpendicular to the first circumference measurement taken, a distance L1. A second circumference measurement—C2—is then taken. This process continues with the user recording the values for L1 through L5 and for C1 through C6. The software tracks variability in the step size as set forth in the patient-specific measurement technique (explained in more detail subsequently).

Figure 3:
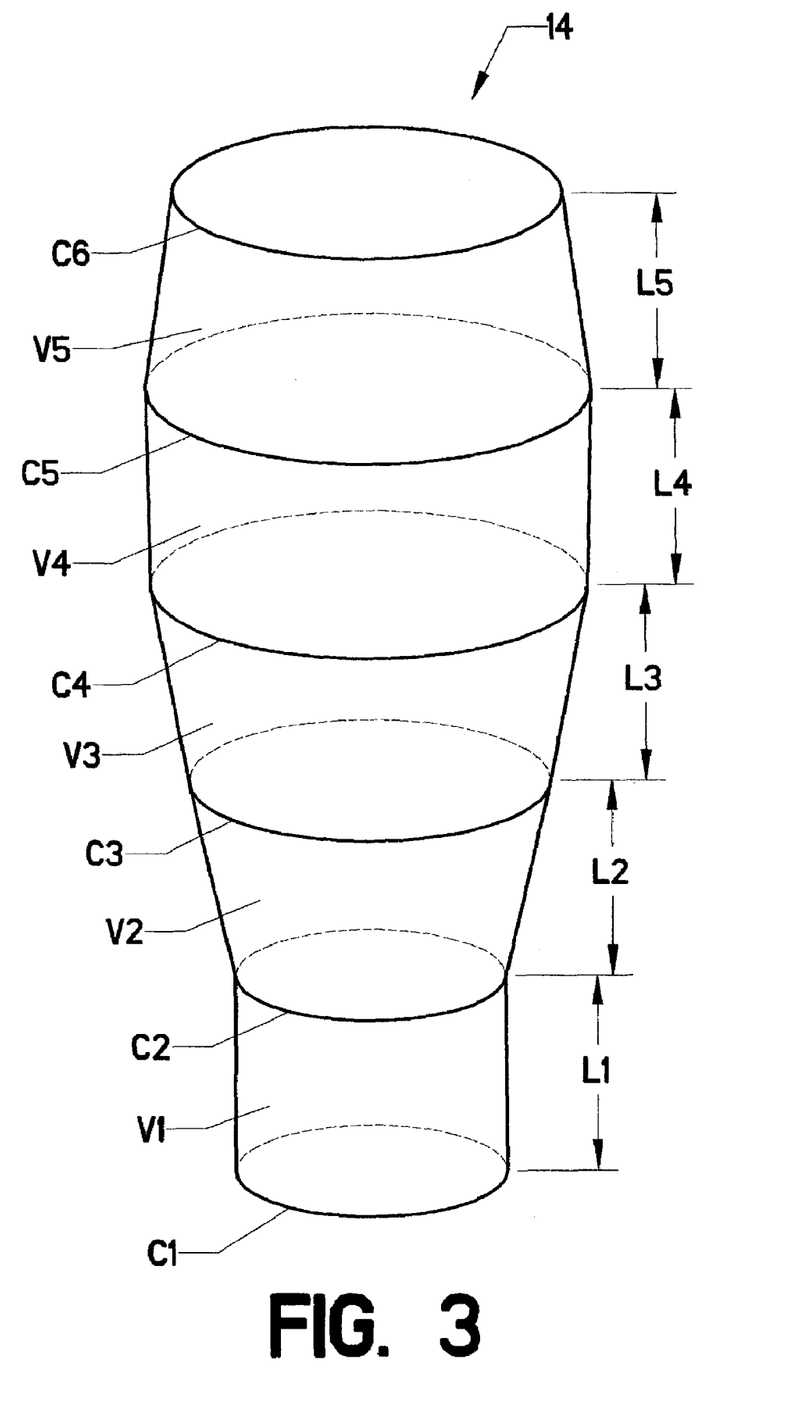
FIG. 3 is an isometric view, showing an example of faceted geometry.

FIG. 3 represents graphically the measurements taken from contoured object 62 in FIG. 2. The regions between the circumference measurements are linearly interpolated to form a stack of truncated cones, each one of which is similar to the one shown in FIG. 1 (denoted as first volume V1 through fifth volume V5). The stack of truncated cones is referred to collectively as faceted volume 14.

Using the same mathematical principles disclosed with respect to the truncated cone of FIG. 1, the volume of volumes V1 through V7 can be calculated. These volumes are then added to find the total volume for faceted volume 14.

Those skilled in the art will know that the volume thus determined is only an approximation of the true volume of contoured object 62. However, if the approach is properly applied, the error will be very small. Of equal significance, since the same technique will be applied during the patient's next visit, any error present will remain relatively constant. Thus, recorded changes will not be the result of variations in the measurement error.

It is customary in the field of mathematical modeling to refer to the distance between each circumference measurement as a "step size." The user taking the measurements can adjust the step size to increase accuracy. Obviously, a smaller step size produces greater accuracy. However, since the measurements are typically taken by hand, a small step size results in much more work. An experienced user can adjust the step size by using small steps in regions where the object's surface is rapidly changing, and larger step sizes in regions where the surface is not rapidly changing. Computer software can be used to track and "remember" a custom step size for a particular patient and body area.

Figure 4:
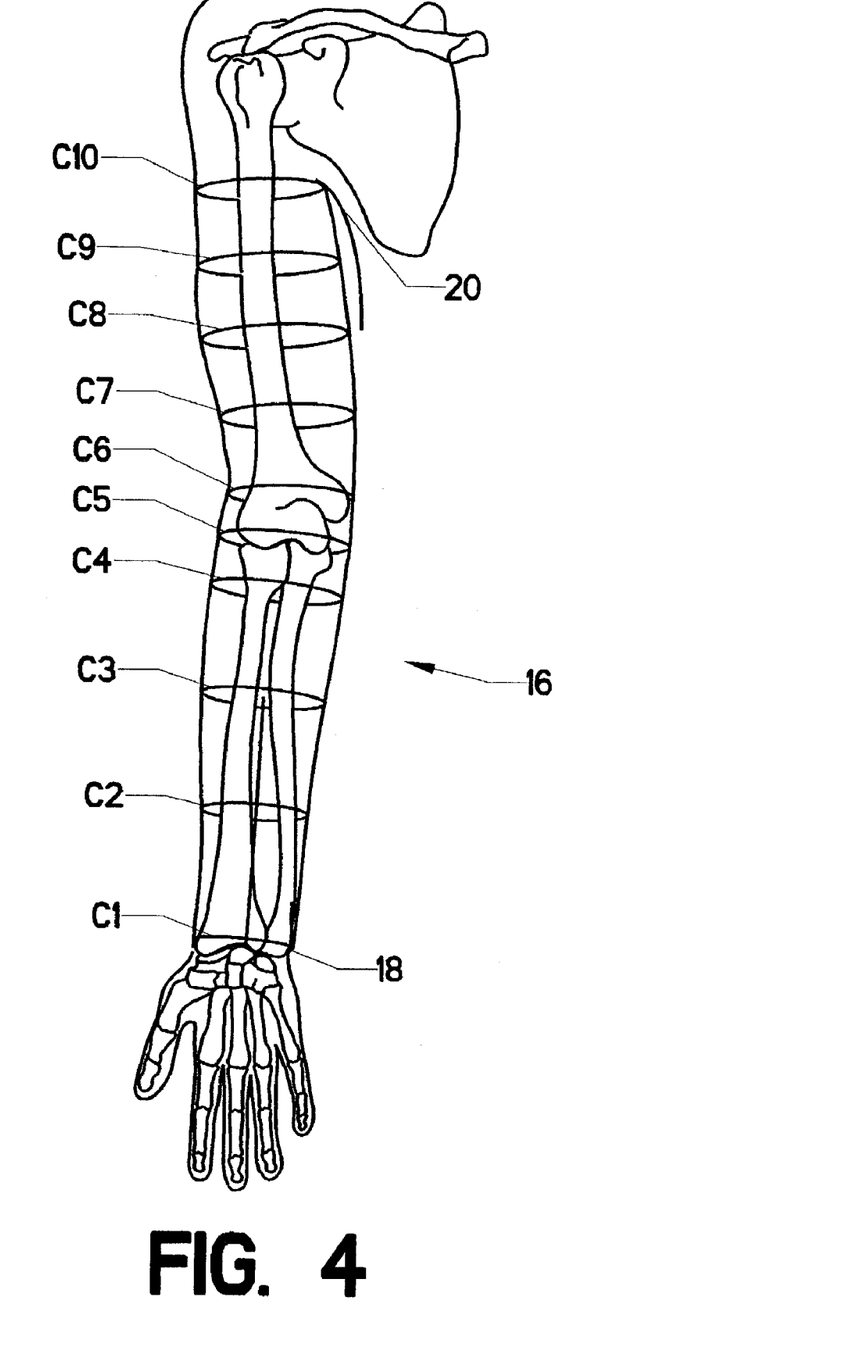
FIG. 4 is a perspective view, showing the application of the present process.

The application of the process to the human body will now be disclosed in detail. FIG. 4 shows the larger structures of arm 16. One key to the proper application of the inventive process is the selection of an anatomical reference point as the origin of the measurements taken. In the case of the human arm, one such reference point is ulna styloid process 18 (other features can be used as a reference on the arm). This feature is a knobby protrusion of the end of the ulna. It can be consistently identified by feeling around the patient's wrist.

Figure 6:
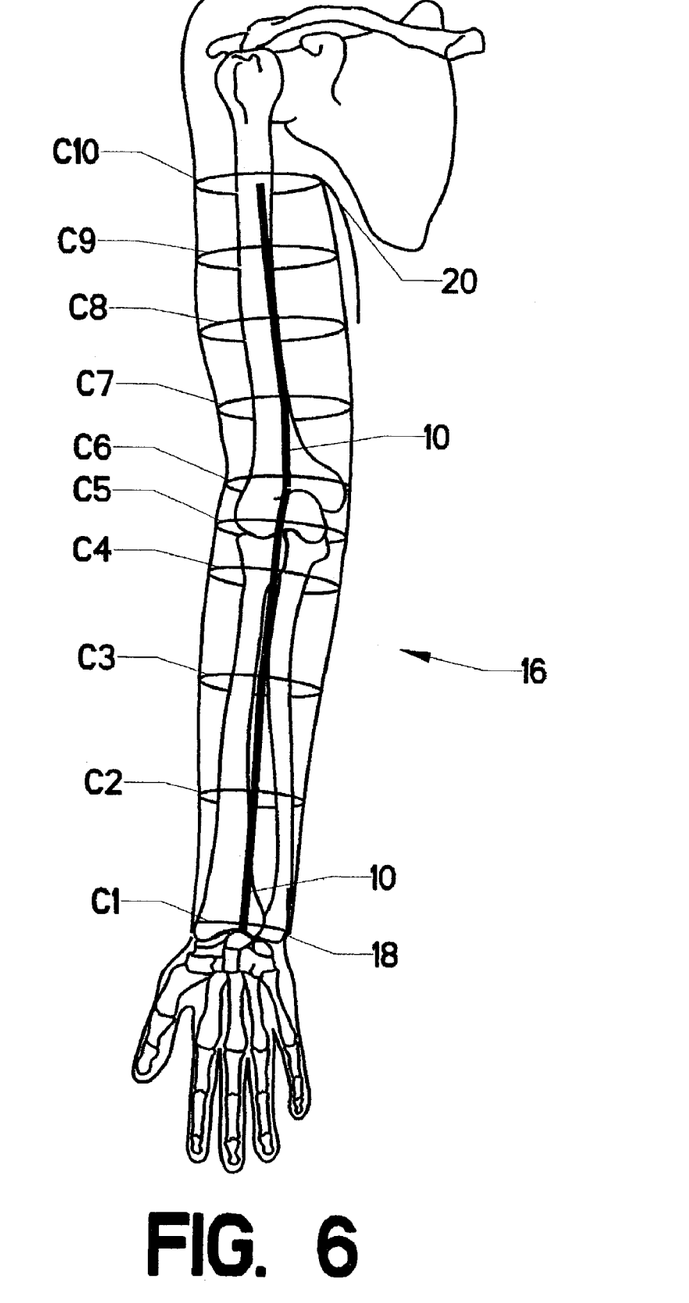
FIG. 6 is a perspective view, showing the application of the present process.

The process allows a clinician to develop a measurement technique which defines the anatomical references for a given patient and assigns a centerline from which the step size will be initiated along the body part. The clinician can deviate the centerline to follow the anatomical contours. FIG. 6 shows centerline 10 as it is adjusted to follow the contours of arm 16. The reader will observe that its course deviates significantly.

In this particular example, the measurements will be taken up to the patient's axilla 20. Returning to FIG. 4, the user begins by measuring first circumference C1. The user then moves up the arm a distance L1 and measures a value for second circumference C2. The user repeats this process for circumferences C3 through C10. The reader will note that the step size has been varied in the course of the measurements. This example represents measurements taken by an experienced clinician. The step size has been reduced in the vicinity of the elbow, where the surface geometry of the arm changes rapidly.

Figure 5:
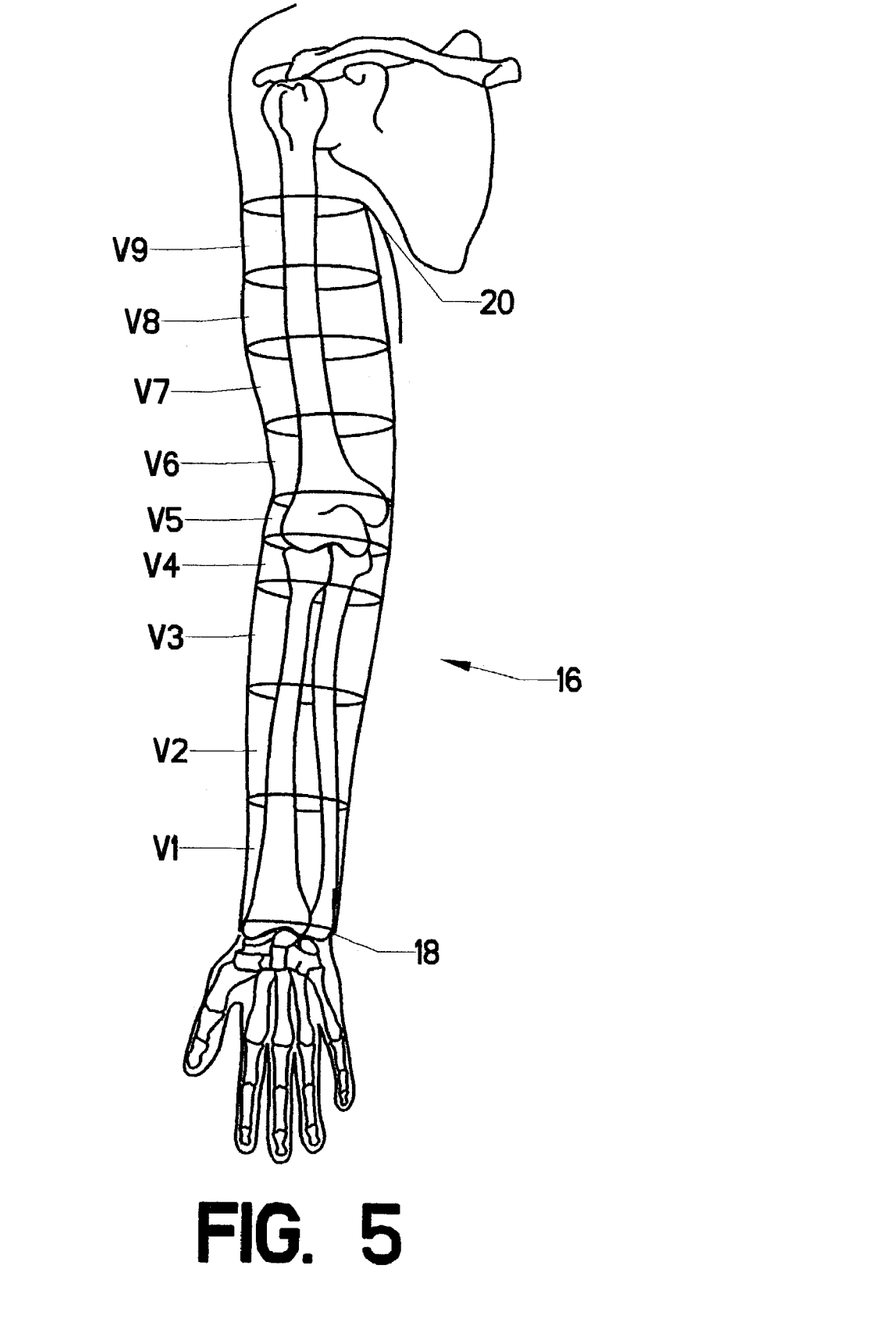
FIG. 5 is a perspective view, showing the application of the present process.

Turning now to FIG. 5, the measurements taken have divided arm 16 into nine discrete volumes—volume V1 through volume V9. The reader will recall that the prior examples used volumes having a central axis; i.e., volumes that were radially symmetric. The human arm is obviously not radially symmetric, nor does its centerline follow a straight path. In FIGS. 4 through 6, it is apparent that the planes defined by the circumference measurements are not parallel. This fact introduces error into the volume caluclations. It is therefore advisable to refine the process somewhat.

FIG. 6 shows the deviations in centerline 10. It graphically depicts a single circumference measurement being taken at the end of each linear segment of centerline 10. The reader will observe that a circumference measurement is taken at the intersection of each linear segment of centerline 10. The use of a single circumference measurement is non-optimal, since such a circumference is not generally perpendicular to both line segments it is adjacent to.

Figure 6B:
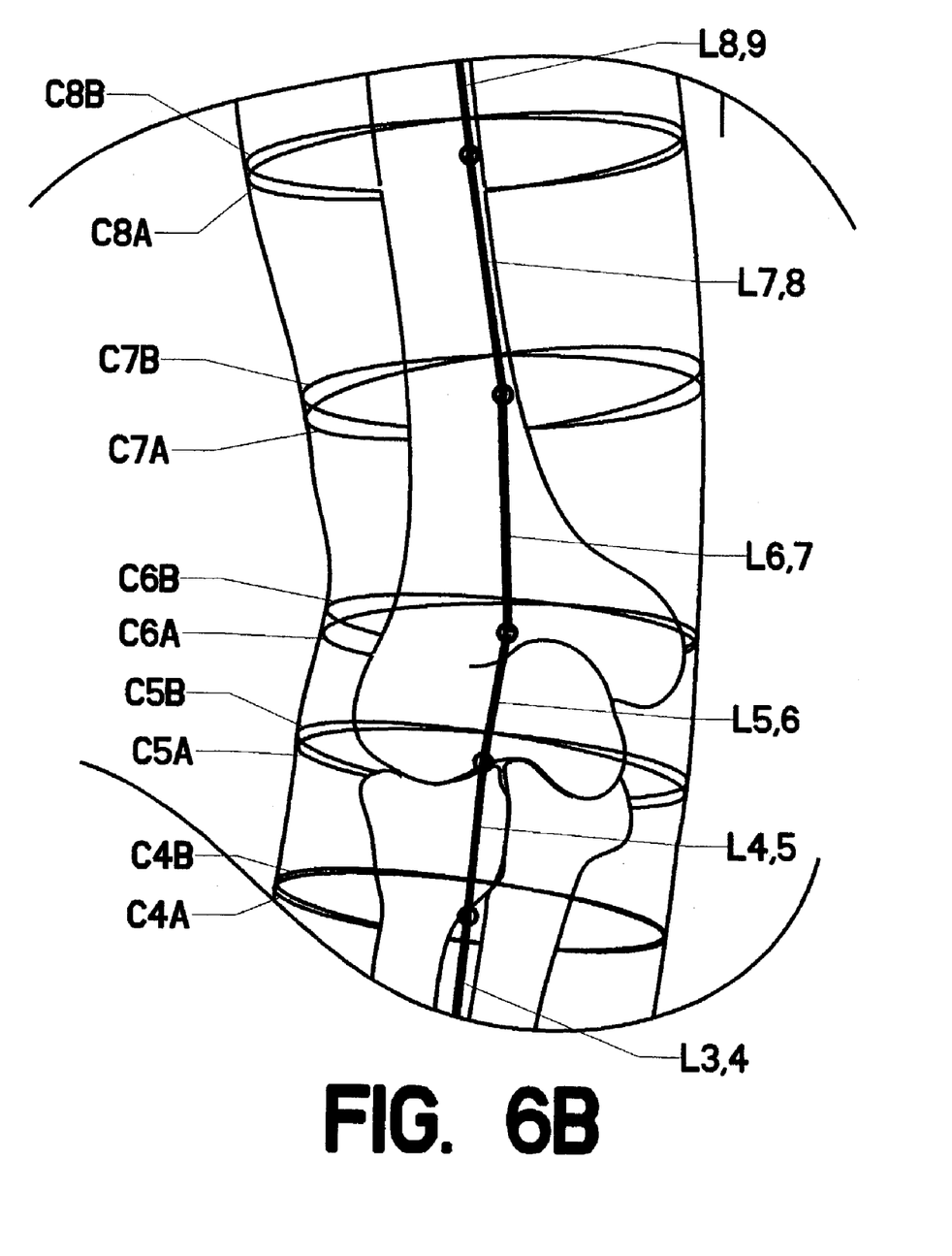
FIG. 6B is a detailed perspective view, showing the application of the present process.

FIG. 6B shows a refinement intended to address this concern. The reader will again observe that centerline 10 is broken into a series of non-aligned linear segments (labeled as "L3,4", "L4,5", and so on). At each intersection point between two segments, it is preferable to take two circumference measurements. For example, at the joint between segment L3,4 and segment L4,5, circumference measurements C4A and C4B are taken. C4A is perpendicular to L3,4 and C4,B is perpendicular to L4,5.

Figure 7:
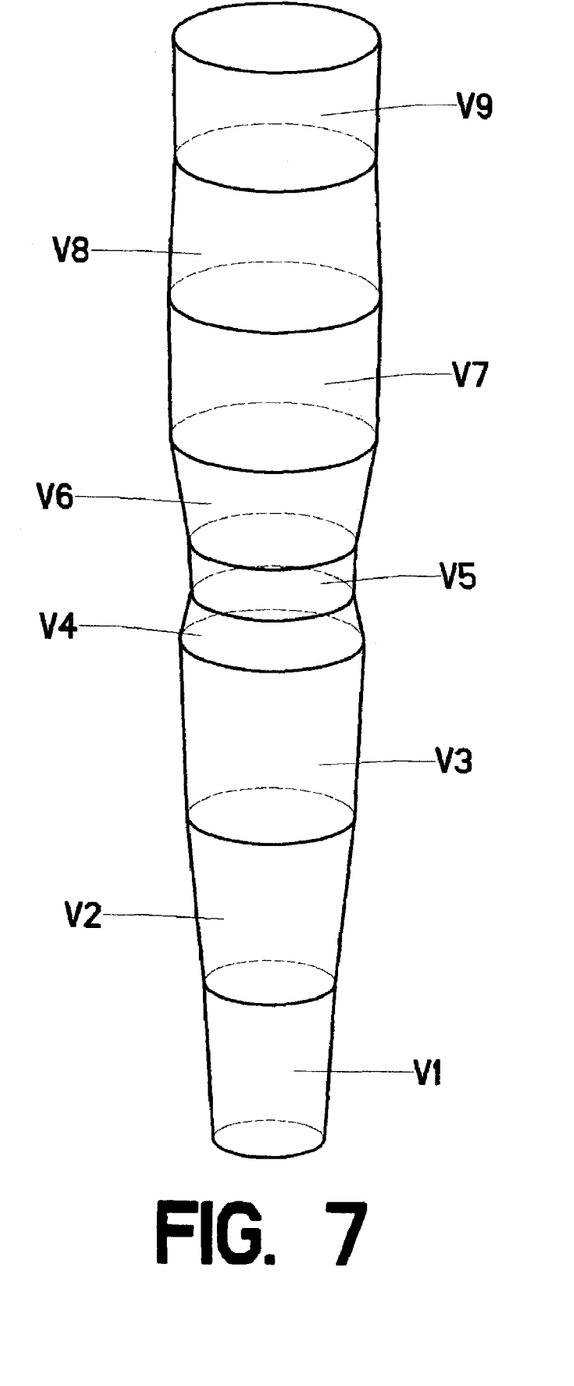
FIG. 7 is an isometric view, showing faceted geometry corresponding to the measurements of a limb.

This approach is easier to see graphically in the two circumference measurements indicated as C6A and C6B (since the centerline deviates its course more radically at that junction). C6A is perpendicular to L5,6, whereas C6B is perpendicular to L6,7. Using this approach, each truncated cone is defined by a linear segment of centerline and two circumference measurements which are perpendicular to that linear segment. As an example, the volume corresponding to L6,7 is calculated using the length L6,7 and circumference measurements C6B and C7A. Thus, it is a true right cone. Error is thereby reduced and any error which is present is maintained more consistently over successive measurements. FIG. 7 shows the results of this approach applied to the entire arm. The arm has been segmented into volumes V1 through V9, with each volume comprising a true truncated right cone.

Figure 8:
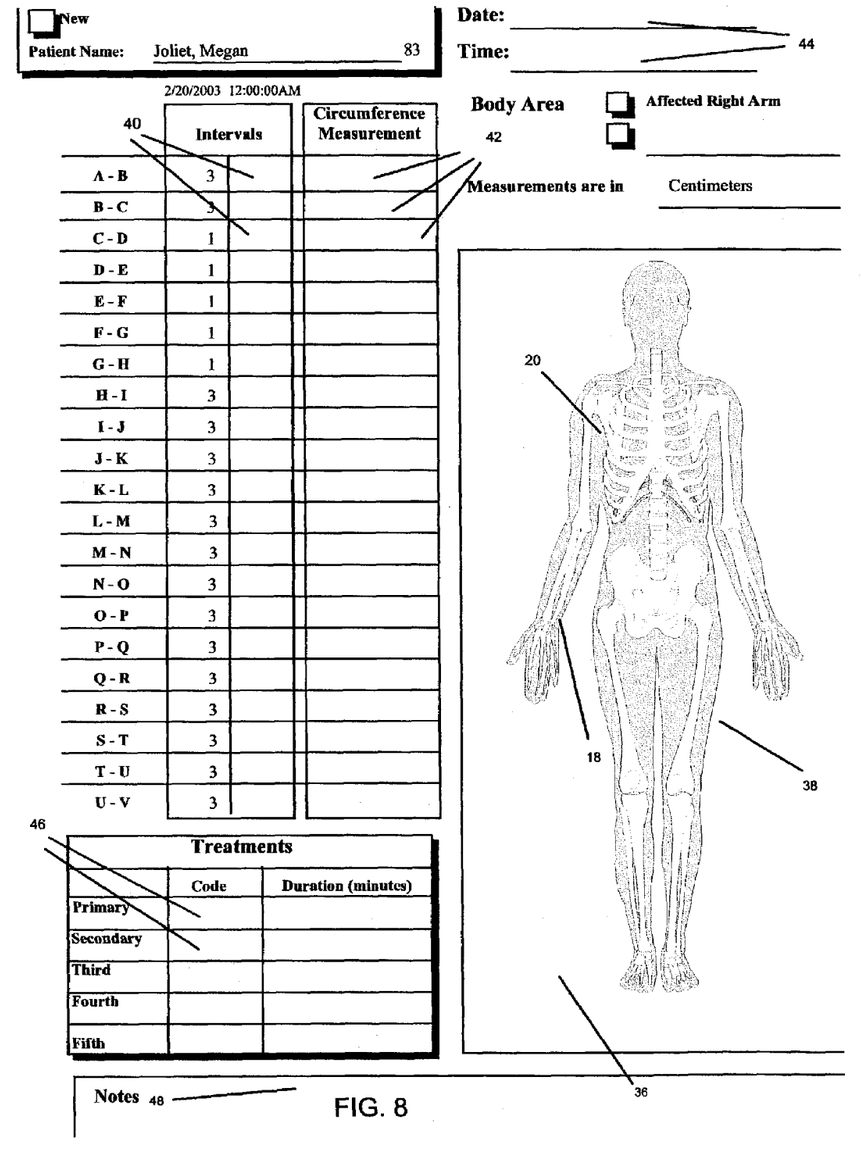
FIG. 8 is a view of a measurement input form.

The most useful function of the process it to allow the clinician to evaluate changes in the volume of a region or regions of a patient over time. Thus, the process contemplates that the measurements described will be repeated over two or more evaluations. The clinician can then evaluate the changes in the volumes and correlate these changes against treatment. Although this entire process can be carried out manually, the use of computer software is obviously advantageous in ensuring greater reliability and reproducibility of the data and the incorporation of other factors into data interpretation. FIG. 8 depicts a user assistance printout from a computer program intended to aid the clinician in carrying out the process (measurement input form 36).

The user selects a body area to evaluate, typically using choices from a pull-down menu. There is no restriction on the body area that can be selected. As examples, the software allows selection of both hands, feet, arms, legs, buttocks, torso, groin, chest, neck, and head. The software displays an image of the selected limb specific to the sex of the patient.

To correspond with the illustrations of FIGS. 4 through 7, the patient's right arm has been selected. The program then graphically depicts suggested anatomical references on physiological reference 38. The user makes certain "picks" to inform the program of which reference points will be used. The user preferably also enters correlative data, such as date/time entry 44, treatment input 48 (describing the history of treatment), and notation input 46 (allowing the addition of observational or other notes).

The user then performs the measurement procedure described previously, entering the values observed as length inputs 40 and circumference inputs 42. The use of the computer program allows the addition of helpful instructions, a graphical depiction of the progress of the measurements along physiological reference 38, and error cross-checking to make sure that the recorded number of lengths and circumferences make sense. The error checking can also evaluate the numbers to detect possible mis-measurements (such as when one circumference is drastically shorter than its neighbors).

Figure 9:
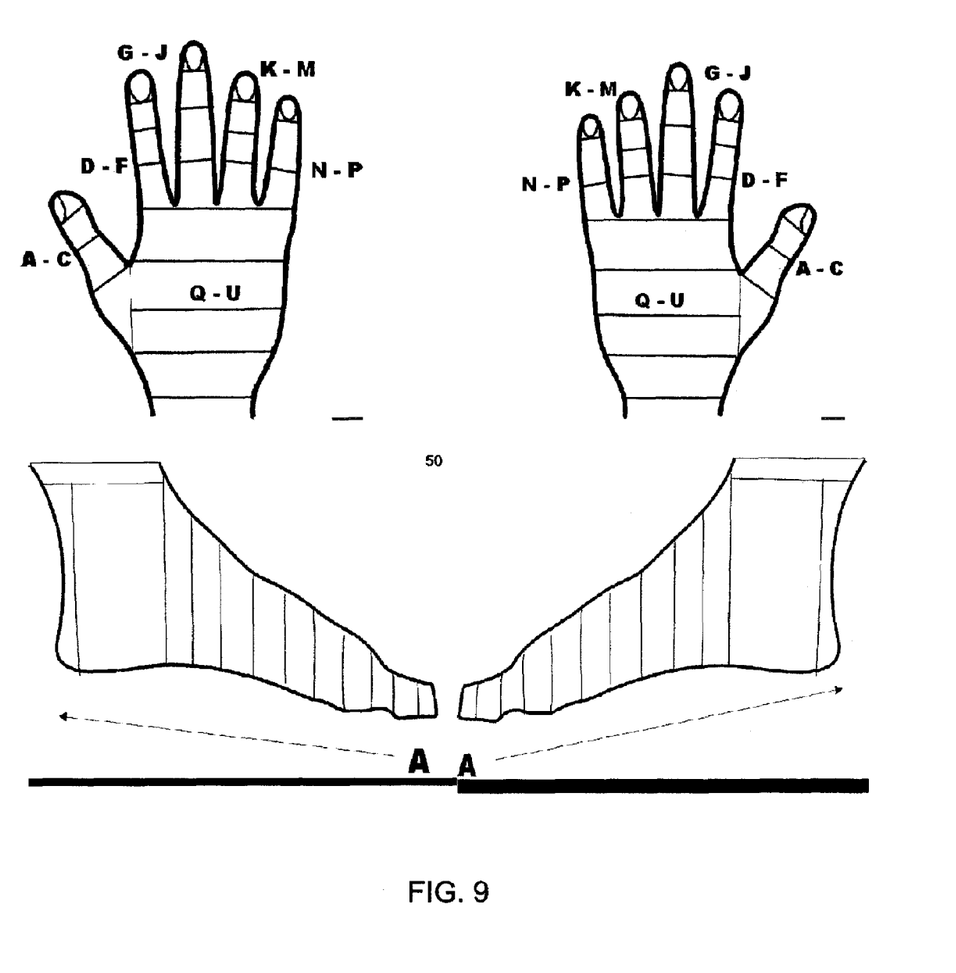
FIG. 9 is a view of a typical measurement guide.

FIG. 9 depicts another helpful display which can be generated by the computer program. If the user has selected a hand or foot to measure, this particular measurement guide 50 can be displayed. Custom intervals or step sizes are also tracked in this software feature. An unlimited number of intervals for all body areas can be tracked. The custom step size or interval aids in the fitting of custom garments made for a patient which are intended to reduce edema.

FIG. 10 shows a display of sample data sheet 52, which displays the data obtained by measuring a patient's arm. Such data sheets would be produced for a series of successive visits. Data sheets present the individualized measurement model created by the clinician, circumference values at patient-specific points, sectional volumes, sectional percent change from previous visits, sectional percent change from first visit, conversion of sectional and total volumes to liters or gallons, total measured body area volumes and total measured body area volumes percent change from previous visits and from first visit. The sheet can also display treatments administered, treatment times, patient notes, and various graphical illustrations. Those skilled in the art will realize that these functions are merely exemplary. Many more could be added.

Figure 11:
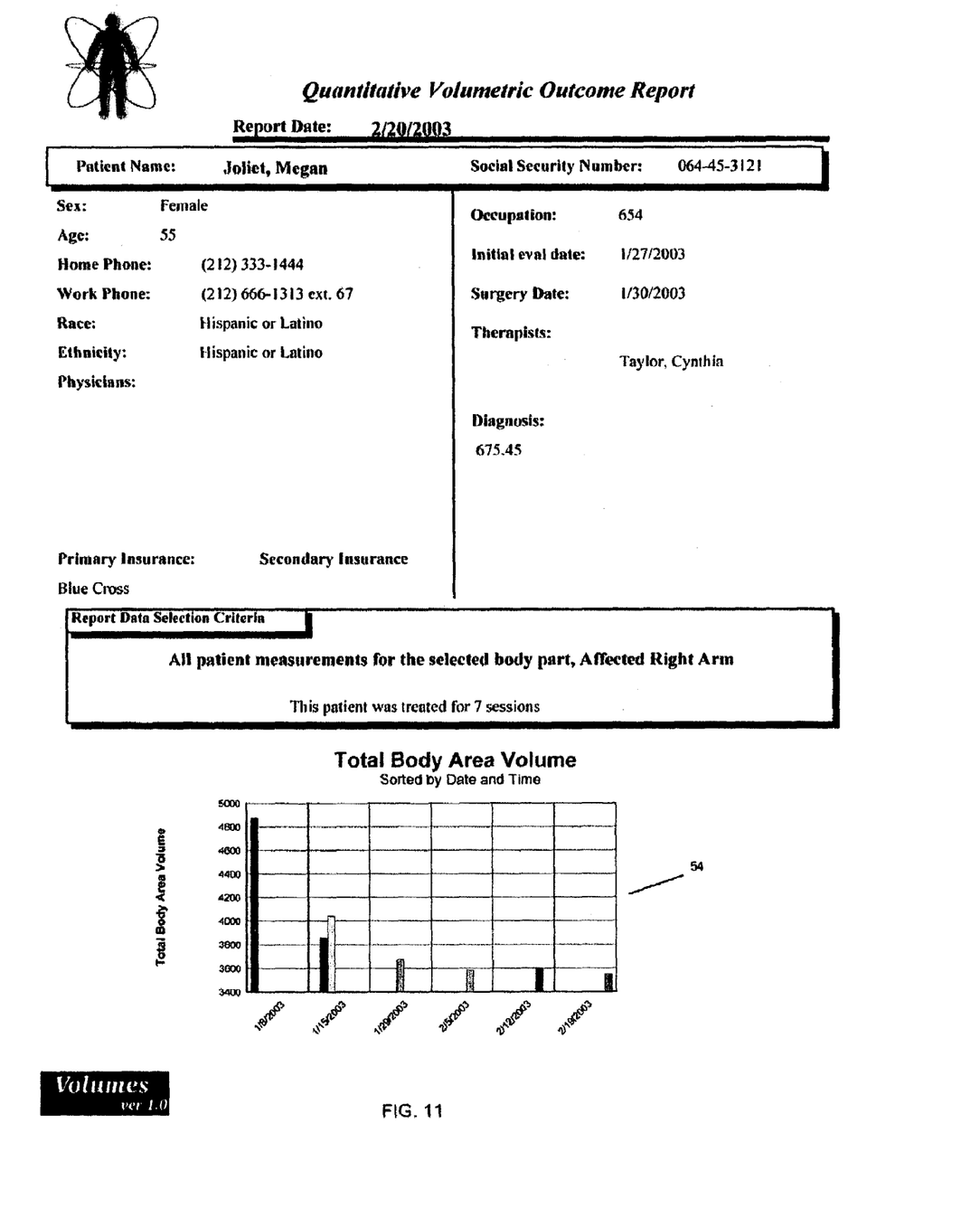
FIG. 11 is a view of a sample graphical presentation of the data.

While it is possible to evaluate volumetric changes using the sample data sheets 52, it may aid understanding to present such data graphically. Again, the use of a computer program can provide this functionality. FIG. 11 shows graphical data presentation 54. This display presents an exemplary graphical "bar chart" showing volumetric changes for a particular patient over time. Such a display allows the practitioner to easily evaluate the efficacy of treatment. Such a display also helps the reader understand why the absolute accuracy of the volume calculation is not nearly as important as the repeatability of the measuring process.

The absolute volume taken on a first evaluation of a patient is not particularly instructive, as variations in human anatomy produce a wide range of volumes for a particular body part. The clinician is much more interested in observing changes in the volume over the course of treatment. Most importantly, the clinician needs to be confident that the changes seen are real and not an artifact of the measurement process. The repeatability of the inventive process herein disclosed greatly reduces the risk of artifact.

Figure 12:
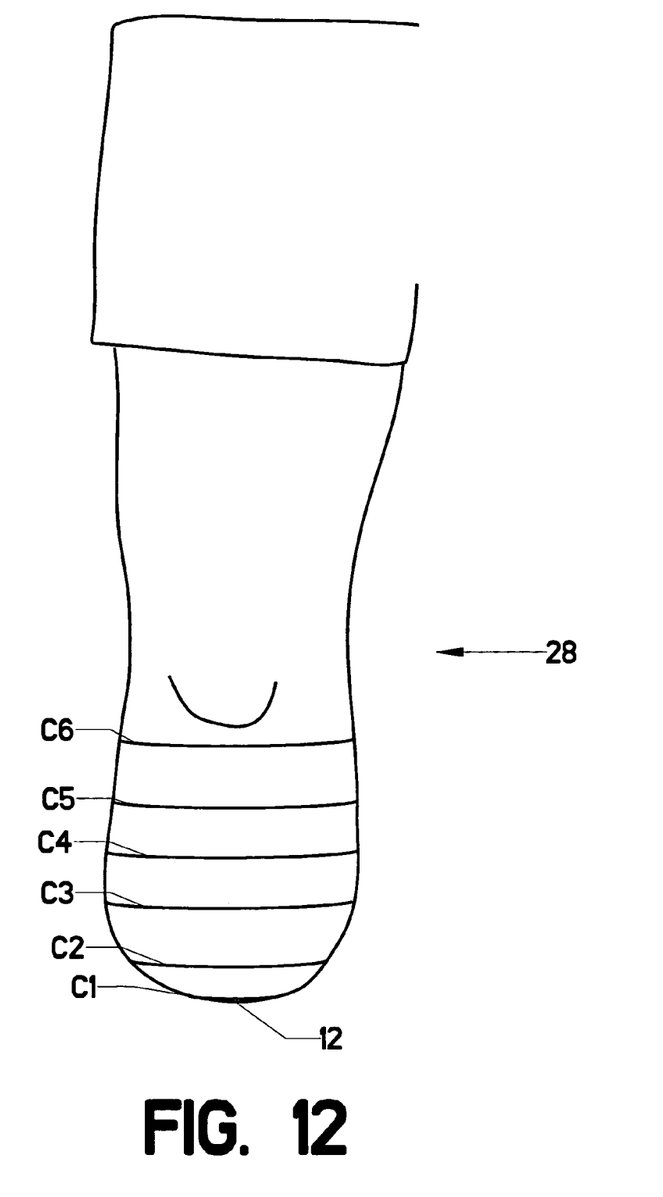
FIG. 12 is an isometric view, showing an atypical limb.
Figure 13:
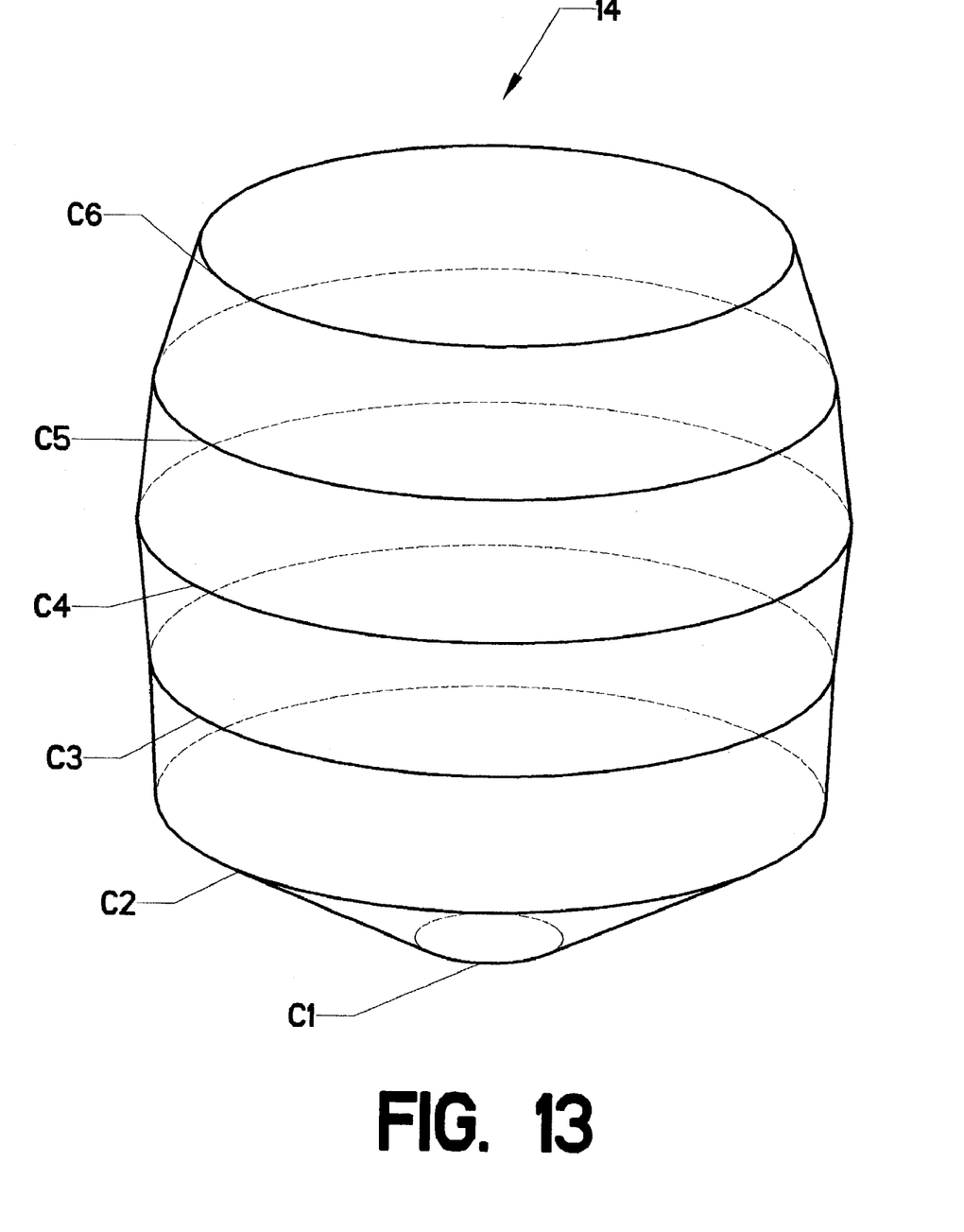
FIG. 13 is an isometric view, showing faceted geometry corresponding to the measurements of the atypical limb.

Further, the process can be employed to measure virtually any type of geometry, even where the patient's anatomy is atypical. FIG. 12 shows a patient having atypical leg 28 (a below-the-knee amputation). The same general process is employed. External starting point 12 is placed at the lower extreme (as may, for example, be recommended by the computer program). A series of circumference measurements C1 through C6 are then taken. These are then used to create faceted volume 14 as shown in FIG. 13. Thus, the reader will appreciate that the inventive process disclosed can be used for virtually any portion of human physiology. The reader will also appreciate that the process can be used to determine the volume of the human body as a whole.

The formatted data sheets guide the clinician in obtaining and recording useful data. This allows the clinician to evaluate the individualized measurement model created for a particular patient, circumference values at specific points, sectional volumes, and sectional percent change from a prior visit. The use of computer software allows the conversion of sectional and total volumes to liters or gallons, a comparison of section volume to total body volume, and numerous other mathematical operations. The software can even guide the clinician in creating comparisons between affected and unaffected regions of the body. As one example, the clinician could be guided to take measurements of a swollen right arm and comparable measurements of the patient's unaffected left arm. The software can even guide the clinician as to desired measurements for specific patient populations on the basis of age, race, diagnosis, and the like. Thus, the software can ask the clinician to collect data which is needed for a populations study—even though the clinician may not be directly aware of the study.

Not all edema is localized. Those skilled in the art will realize that the methods disclosed for computing the volume of a selected portion of a patient can also be used to compute a volume for the entire patient. The clinician need only record the measurements for all regions of the patient's body. This data can then be used to monitor changes in the volume of the entire patient over subsequent visits.

The preceding description contains significant detail regarding the novel aspects of the present invention. It is should not be construed, however, as limiting the scope of the invention but rather as providing illustrations of the preferred embodiments of the invention. As an example, the computer interface illustrations are but one type of many possible types well known to those skilled in the art. Thus, the scope of the invention should be fixed by the following claims, rather than by the examples given.

I claim:

1. A method for analyzing approximations of the volume of a chosen portion of a patient to determine the presence or absence of edema, comprising:
   a. establishing an external starting point using a fixed anatomical reference within or adjacent to said chosen portion;
   b. measuring a first circumference at said external starting point;
   c. recording said measurement of said first circumference;
   d. moving a user-selected first fixed distance along said chosen portion and measuring a second circumference;
   e. recording said first fixed distance and said measurement of said second circumference;
   f. continuing to move along said chosen portion in a series of variable user-selected fixed distances, taking a circumference measurement at each stopping point;
   g. recording said fixed distances and said measurements of said circumferences until the entire length of said chosen portion has been measured; and
   h. using said recorded fixed distances and circumference measurements to compute said volume of said chosen portion for a first time as a series of truncated cones, thereby determining an approximate volume for said chosen portion of said patient.

2. The method as recited in claim 1, further comprising:
   a. repeating all the steps of claim 1 at a second time which is later than said first time, including computing a second volume for said chosen portion at said second time; and
   b. comparing said second volume computed at said second time to said original computed volume computed at said first time in order to determine the change in volume of said chosen portion.

3. A method as recited in claim 2, further comprising correlating said change in said volume of said chosen portion to medical treatment given to said patient.

4. A method as recited in claim 1, wherein said fixed distances and said circumference measurements are entered into a computer, said computer associated with a computer program, and wherein said computer program directs said computer to compute said volume of said chosen portion.

5. A method as recited in claim 2, wherein:
   a. a computer is used to record said fixed distances and said circumference measurements;
   b. a computer program associated with said computer is used to direct said computer to compute said original volume and said second volume; and
   c. said computer program associated with said computer is used to direct said computer to compute the difference between said original volume and said second volume.

6. A method as recited in claim 3, wherein a computer program associated with a computer is used to direct said computer to record said medical treatment given to said patient and to correlate said medical treatment to said change in volume.

7. A method as recited in claim 3, wherein said process is applied to a plurality of patients and wherein a computer program associated with a computer is used to direct said computer to analyze said plurality of patients in order to determine a result selected from the group comprising: the efficacy of treatments applied to said plurality of patients, the relationship of edema to diagnoses applied to said plurality of patients, the correlation between edema and the occupations of said plurality of patients, the correlation between edema and the geographic origins of said plurality of patients, the correlation between edema and the sex of said plurality of patients, the correlation between edema and the race of said plurality of patients, and the correlation between edema and the ethnicity of said plurality of patients.

8. A method as recited in claim 2, wherein a volume for the entire body of said patient is computed at said first time.

9. A method as recited in claim 8, wherein a computer program associated with a computer is used to direct said computer to calculate a change in said volume computed for the entire body of said patient from said first time to said second time.

10. A method for analyzing approximations of the volume of a chosen portion of a patient to make a determination of the presence or absence of edema, comprising:
   a. establishing an external starting point using a fixed anatomical reference within or adjacent to said chosen portion;
   b. measuring a first circumference at said external starting point;
   c. recording said measurement of said first circumference;
   d. moving a user-selected first fixed distance along said chosen portion and measuring a second circumference;
   e. recording said first fixed distance and said measurement of said second circumference;

f. continuing to move along said chosen portion in a series of variable user-selected fixed distances, taking a circumference measurement at each stopping point;
g. recording said fixed distances and said measurements of said circumferences until the entire length of said chosen portion has been measured;
h. using said recorded fixed distances and circumference measurements to compute said volume of said chosen portion for a first time as a series of truncated cones;
i. using said volume computed in steps a through h to make said determination of the presence or absence of edema.

11. The method as recited in claim 1, further comprising:
a. repeating all the steps a through h of claim 10 at a second time which is later than said first time, including computing a second volume for said chosen portion at said second time; and
b. comparing said second volume computed at said second time to said original computed volume to make said determination of the presence or absence of edema.

\* \* \* \* \*